(12) United States Patent
Yang

(10) Patent No.: US 11,686,927 B2
(45) Date of Patent: Jun. 27, 2023

(54) SLIM IMMERSIVE DISPLAY DEVICE AND SLIM VISUALIZATION DEVICE

(71) Applicant: ELECTRONICS AND TELECOMMUNICATIONS RESEARCH INSTITUTE, Daejeon (KR)

(72) Inventor: Ung-Yeon Yang, Daejeon (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 0 days.

(21) Appl. No.: 17/411,716

(22) Filed: Aug. 25, 2021

(65) Prior Publication Data

US 2022/0066185 A1 Mar. 3, 2022

(30) Foreign Application Priority Data

Aug. 26, 2020 (KR) .................. 10-2020-0108031
Jul. 29, 2021 (KR) .................. 10-2021-0099909

(51) Int. Cl.
| | | |
|---|---|---|
| *G02B 7/12* | (2021.01) | |
| *G06F 3/14* | (2006.01) | |
| *G06T 11/00* | (2006.01) | |
| *G09B 9/00* | (2006.01) | |
| *G06V 10/10* | (2022.01) | |
| *G06V 20/20* | (2022.01) | |
| *A62B 7/02* | (2006.01) | |
| *G02B 17/08* | (2006.01) | |
| *G02B 5/30* | (2006.01) | |

(Continued)

(52) U.S. Cl.
CPC ........ *G02B 17/0808* (2013.01); *A61B 5/7445* (2013.01); *G02B 5/3083* (2013.01); *G02B 7/12* (2013.01); *G06F 3/14* (2013.01); *G06F 18/214* (2023.01); *G06T 11/00* (2013.01); *G06V 10/10* (2022.01); *G06V 20/20* (2022.01); *G09B 9/00* (2013.01); *A62B 7/02* (2013.01); *A62C 99/0081* (2013.01)

(58) Field of Classification Search
CPC .. G02B 17/0808; G02B 5/3083; G06V 20/20; G06V 10/10; A61B 5/7445; G06F 3/14; G06K 9/6256; G06T 11/00; G09B 9/00
USPC ........................................................ 345/619
See application file for complete search history.

(56) References Cited

U.S. PATENT DOCUMENTS

| 9,760,168 B2 | 9/2017 | Sugimoto |
|---|---|---|
| 10,969,592 B2 | 4/2021 | Hua et al. |

(Continued)

FOREIGN PATENT DOCUMENTS

| JP | 2014-093036 A | 5/2014 |
|---|---|---|
| JP | 2020-519964 A | 7/2020 |

(Continued)

*Primary Examiner* — Hai Tao Sun

(57) ABSTRACT

Disclosed herein are a slim immersive display device and a slim visualization device. The slim immersive display device includes a slim visualization module for forming an image on a retina of an eyeball of a user based on an externally input image signal, a state information acquisition unit for acquiring a state of an external device as a state image, and a content control unit for analyzing the state image, generating an image corresponding to virtual-reality environment information, and inputting the image to the slim visualization module.

13 Claims, 12 Drawing Sheets

(51) Int. Cl.
    *A61B 5/00*     (2006.01)
    *G06F 18/214*     (2023.01)
    *A62C 99/00*     (2010.01)

(56)     References Cited

U.S. PATENT DOCUMENTS

| | | |
|---|---|---|
| 11,002,959 B2 | 5/2021 | Yi et al. |
| 11,054,622 B1 * | 7/2021 | Collier ............... G02B 27/0172 |
| 11,630,291 B2 | 4/2023 | Etter et al. |
| 2016/0028947 A1 * | 1/2016 | Wexler ................. G06F 3/0304 |
| | | 348/372 |
| 2016/0363763 A1 | 12/2016 | Yang et al. |
| 2017/0227770 A1 * | 8/2017 | Carollo ............. G02B 27/0172 |
| 2017/0357333 A1 | 12/2017 | Balan et al. |
| 2018/0075659 A1 * | 3/2018 | Browy ................. G02B 27/017 |
| 2018/0150690 A1 | 5/2018 | Yin |

FOREIGN PATENT DOCUMENTS

| | | |
|---|---|---|
| KR | 10-2011-0104286 A | 9/2011 |
| KR | 10-2016-0147494 A | 12/2016 |
| KR | 10-1875313 B1 | 6/2018 |
| KR | 10-2018-0097947 A | 9/2018 |
| KR | 1020180133937 A | 12/2018 |
| KR | 1020190089912 A | 7/2019 |
| KR | 1020190094270 A | 8/2019 |
| KR | 10-2020-0046435 A | 5/2020 |

\* cited by examiner

SLIM IMMERSIVE DISPLAY DEVICE AND SLIM VISUALIZATION DEVICE

CROSS REFERENCE TO RELATED APPLICATIONS

This application claims the benefit of Korean Patent Application Nos. 10-2020-0108031, filed Aug. 26, 2020 and 10-2021-0099909, filed Jul. 29, 2021, which are hereby incorporated by reference in their entireties into this application.

BACKGROUND OF THE INVENTION

1. Technical Field

The following embodiments relate generally to user interface technology used in the fields of Virtual Reality (VR), Augmented Reality (AR), and Mixed Reality (MR).

2. Description of the Related Art

As a representative user interface used to realistically represent personal experiences based on freely set viewpoints, for example, six Degrees of Freedom (6DOF) in the Virtual Reality (VR), Augmented Reality (AR), and Mixed Reality (MR) fields, there is a Head-Mounted Display (HMD), which is an immersive display device.

However, the quality of a current HMD does not reach the level at which the same realistic presence as a user's visual experience in the actual environment can be implemented. Due thereto, when the user undergoes virtual training while wearing the HMD, the user may clearly recognize the difference between the real environment and the virtual environment, and thus it is difficult to anticipate a desired training effect resembling hands-on training due to the deteriorated virtual presence.

As a representative cognitive element causing the deterioration of presence in virtual space, there is a problem of mismatched field of view (viewing angle). That is, because an optical system of a conventional fully immersive display (HMD) is fixed according to specific eyesight conditions, there is a limitation in that a separate accessory required for eyesight correction for users having different visual capabilities must be used.

Also, since the current HMD is implemented in a form provided with a head-mounted portion having a considerable volume and weight so as to improve the sensation of visual immersion, the user experience in a virtual training situation is different from that of the real environment due to the volume and weight of the HMD, to which the user is not subjected in the real environment.

When a virtual training system is developed, sense-synchronization technology that produces the same stimulus as that on site so as to enable a training environment to be constructed in virtual space without interfering with a user experience through a user interface on site is required in order to accommodate the basic design rule of a training system, stipulating that "the capability learned by experience in a training process must be able to be equally utilized on site without awkwardness". However, as described above, an existing user display interface has a limitation in that it cannot realize 100% of physical phenomena occurring between the environment formed in a human visual sensory organ and a sense recognition organ.

Meanwhile, virtual-reality firefighting training has a limitation in that it is difficult for the user to realistically emulate 100% of corresponding functions so as to obtain a feedback on his or her situation, such as the remaining amount of air in a respirator and biometric signals, at the level of a real environment rather than a virtual environment, through an experience (training) program. Also, a respirator used for safety during emergencies, disaster response, and execution of safety-related duties has a large difference with regard to the duration in which a breathing air cylinder (e.g., air tank), having a predetermined specification, is used by different persons.

Therefore, in order to secure the safety of users on site, optimization training for maximizing the durations for which individual persons are capable of utilizing the respirator through a series of repeated training procedures is required. For this training, users must practice training while utilizing realistic equipment such as the respirator in conjunction with virtual content for virtual training. However, because various types of respirators may be used, monitoring instruments for measuring the remaining amount of air in each respirator include various schemes, such as an analog scheme and a digital scheme, and respirators have various shapes, international standards for respirators are currently insufficient, thus resulting in a large number of difficulties in synchronizing the states of equipment actually provided on site with virtual-reality content in association with the virtual-reality content.

SUMMARY OF THE INVENTION

An embodiment is intended to improve a wearing sensation by reducing the volume and the weight of a display device, thus preventing the display device from interfering with an experience resembling an actual situation on site, with the result that the visual field of view may be increased.

An embodiment is intended to provide the best image quality to the user of a virtual training system in consideration of human engineering characteristics based on visual sensory organs.

An embodiment is intended to provide a general-purpose connection interface which supports a training system so as to represent state information of a user in virtual-reality content based on information on the state of realistic equipment so that a highly realistic training system can be operated using equipment that is employed on site.

In accordance with an aspect, there is provided a slim visualization device, including a display panel configured to output an externally input image signal, and an optical unit manufactured using at least two refractive lenses and configured to refract and reflect straight-traveling visible light corresponding to an image output via the display panel through the at least two refractive lenses, thus forming the image on a retina of an eyeball of a user.

The optical unit may include a first lens having a first surface facing the retina of the eyeball of the user, and a second lens having a first surface facing a second surface of the first lens and a second surface facing the display panel, wherein a curvature of the first surface of the first lens may be less than a curvature of the second surface of the first lens, and a curvature of the second surface of the second lens may be less than a curvature of the first surface of the second lens.

The optical unit may be configured such that the visible light corresponding to the image output via the display panel is primarily refracted while sequentially passing through the second lens and the first lens, the primarily refracted visible light is reflected from the first surface of the first lens, and is secondarily refracted while sequentially passing through the first lens and the second lens, and the secondarily refracted visible light is reflected from the second surface of the second lens, is tertiarily refracted while sequentially passing through the second lens and the first lens, and is then delivered to a pupil of the user.

The optical unit may further include a polarizer disposed between the display panel and the second lens, a quarter-wave plate disposed between the polarizer and the second lens, a quarter-wave plate disposed between the second lens and the first lens, and a linear polarizer disposed between the first lens and the retina of the eyeball of the user.

The display panel and the optical unit may be implemented as an integrated module, and the integrated module may be separated into a left-eye module and a right-eye module to correspond to a left eye and a right eye, respectively The slim visualization device may further include an interpupillary distance adjustment unit for adjusting a distance between the left-eye module and the right-eye module.

The slim visualization device may further include an interpupillary angle adjustment unit for adjusting a joint angle between the right-eye module and the left-eye module.

The joint angle between the right-eye module and the left-eye module may be adjusted to correspond to (to match) characteristics of the body structure of the user who wears the display device (a human factor related to a binocular eyeball arrangement structure).

In accordance with another aspect, there is provided a slim immersive display device, including a slim visualization module for forming an image on a retina of an eyeball of a user based on an externally input image signal, a state information acquisition unit for acquiring a state of an external device as a state image, and a content control unit for analyzing the state image, generating an image corresponding to virtual-reality environment information, and inputting the image to the slim visualization module.

The state information acquisition unit may include a coupling unit attached/detached to/from an information output unit for sensing the external device, and an image acquisition unit for acquiring a short-range image of the information output unit for sensing the external device.

The coupling unit is made of a magnet and a flexible material to facilitate attachment/detachment.

The content control unit may include an image information recognition unit configured to be learned in advance based on state images for respective product types of an information output unit for sensing the external device, and to recognize information on the external device from the state image input from the state information acquisition unit, wherein the state image is the state image of the information output unit for sensing the external device, a training management unit for updating a state of a virtual object in virtual-reality content with a result of simulating a function of the virtual object based on information on the external device recognized by the image information recognition unit, and a virtual-reality processing unit for processing image information of the content, in which the state of the virtual object is updated, as virtual-reality image information, and outputting the processed virtual-reality image information to the slim visualization module.

The state information acquisition unit may further acquire a state image of an information output unit for collecting biometric signal information of the user, and the content control unit may incorporate the biometric signal information of the user into the virtual-reality content.

The slim visualization module may include a display panel configured to output the externally input image signal, and an optical unit manufactured using at least two refractive lenses and configured to refract and reflect straight-traveling visible light corresponding to an image output via the display panel through the at least two refractive lenses, thus forming the image on the retina of the eyeball of the user.

The optical unit may include a first lens having a first surface facing the retina of the eyeball of the user, and a second lens having a first surface facing a second surface of the first lens and a second surface facing the display panel, wherein a curvature of the first surface of the first lens may be less than a curvature of the second surface of the first lens, and a curvature of the second surface of the second lens may be less than a curvature of the first surface of the second lens.

The optical unit may further include a polarizer disposed between the display panel and the second lens, a quarter-wave plate disposed between the polarizer and the second lens, a quarter-wave plate disposed between the second lens and the first lens, and a linear polarizer disposed between the first lens and the retina of the eyeball of the user.

The display panel and the optical unit may be implemented as an integrated module, and the integrated module may be separated into a left-eye module and a right-eye module to correspond to a left eye and a right eye, respectively.

The slim visualization module may further include an interpupillary distance adjustment unit for adjusting a distance between the left-eye module and the right-eye module.

The slim visualization module may further include an interpupillary angle adjustment unit for adjusting a joint angle between the right-eye module and the left-eye module.

In accordance with a further aspect, there is provided a slim immersive display device, including a slim visualization module for forming an image on a retina of an eyeball of a user based on an externally input image signal, a state information acquisition unit for acquiring a state image of an information output unit for sensing an external device, and a content control unit for analyzing the state image, generating an image corresponding to virtual-reality environment information, and inputting the image to the slim visualization module, wherein the slim visualization module may include a display panel configured to output the externally input image signal, and an optical unit manufactured using at least two refractive lenses and configured to refract and reflect straight-traveling visible light corresponding to an image output via the display panel through the at least two refractive lenses, thus forming the image on the retina of the eyeball of the user.

The content control unit may include an image information recognition unit configured to be learned in advance based on state images for respective product types of the information output unit for sensing the external device, and to recognize information on the external device from the state image input from the state information acquisition unit, wherein the state image is the state image of the information output unit for sensing the external device, a training management unit for updating a state of a virtual object in virtual-reality content with a result of simulating a function of the virtual object based on information on the external device recognized by the image information recognition unit, and a virtual-reality processing unit for processing image information of the content, in which the state of the virtual object is updated, as virtual-reality image information, and outputting the processed virtual-reality image information to the slim visualization module.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
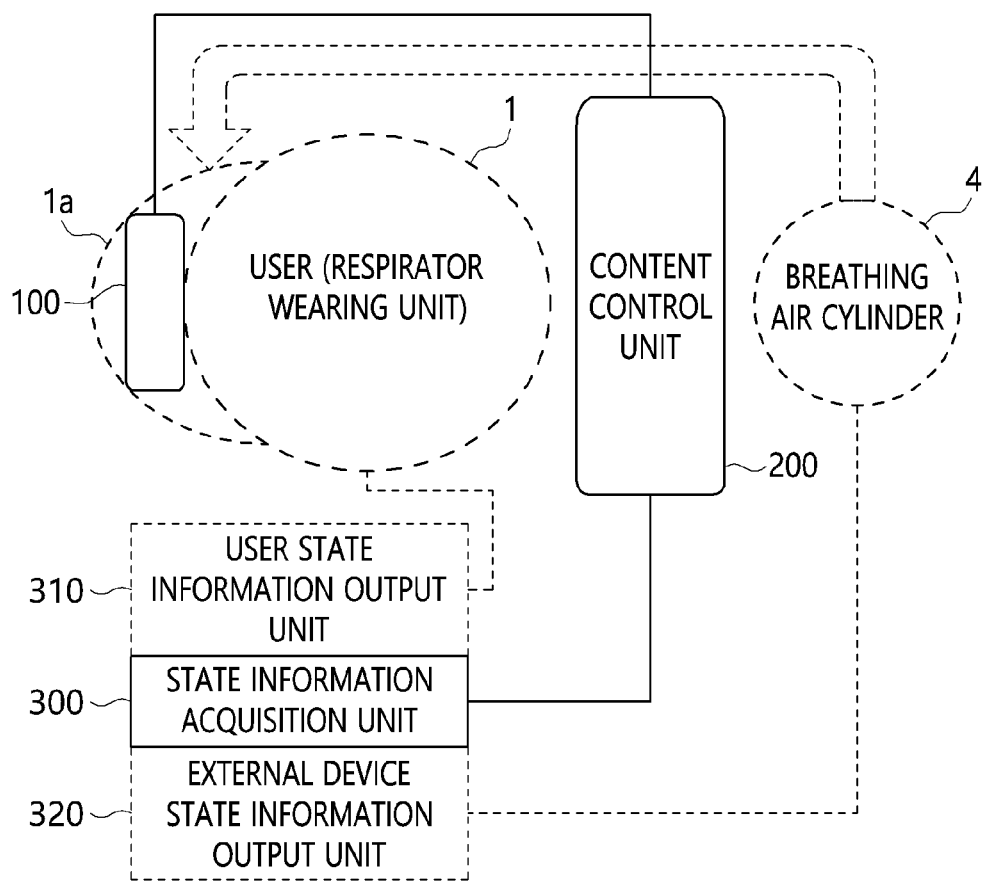
FIG. 1 is a schematic configuration diagram of a slim immersive display device according to an embodiment.

Advantages and features of the present invention and methods for achieving the same will be clarified with reference to embodiments described later in detail together with the accompanying drawings. However, the present invention is capable of being implemented in various forms, and is not limited to the embodiments described later, and these embodiments are provided so that this invention will be thorough and complete and will fully convey the scope of the present invention to those skilled in the art. The present invention should be defined by the scope of the accompanying claims. The same reference numerals are used to designate the same components throughout the specification.

It will be understood that, although the terms "first" and "second" may be used herein to describe various components, these components are not limited by these terms. These terms are only used to distinguish one component from another component. Therefore, it will be apparent that a first component, which will be described below, may alternatively be a second component without departing from the technical spirit of the present invention.

The terms used in the present specification are merely used to describe embodiments, and are not intended to limit the present invention. In the present specification, a singular expression includes the plural sense unless a description to the contrary is specifically made in context. It should be understood that the term "comprises" or "comprising" used in the specification implies that a described component or step is not intended to exclude the possibility that one or more other components or steps will be present or added.

Unless differently defined, all terms used in the present specification can be construed as having the same meanings as waits generally understood by those skilled in the art to which the present invention pertains. Further, terms defined in generally used dictionaries are not to be interpreted as having ideal or excessively formal meanings unless they are definitely defined in the present specification.

An embodiment relates to a slim immersive display device which allows a user to have the same experience as an actual situation on site, and the slim immersive display device according to the embodiment may be applied to a Head-Mounted Display (HMD) for virtual reality firefighting training in which a firefighter undergoes an individual experience and collaborative training in virtual space. However, this is only an example for helping better understanding of the present invention, and the present invention is not limited thereto. That is, the slim immersive display device according to the embodiment may be used in various types of content to which not only virtual-reality firefighting training but also Virtual Reality (VR), Augmented Reality (AR), and Mixed Reality (MR) are applied.

FIG. 1 is a schematic configuration diagram of a slim immersive display device according to an embodiment.

Referring to FIG. 1, the slim immersive display device according to the embodiment may be used together with realistic equipment, such as a face-mounted respirator 1 and a breathing air cylinder (storage) 4 located on the body of a user, and may then be utilized for virtual-reality training.

In detail, the slim immersive display device may include a slim visualization module 100, a content control unit 200, and a state information acquisition unit 300.

The slim visualization module 100 forms an image on the retina of the eyeball of the user based on an externally input image signal. In an embodiment, the slim visualization module 100 is characterized in that an optical path from a display panel to the eyeball of the user is shortened using at least two refractive lenses so that the slim visualization module 100 is provided in internal space 1a of the user's respirator wearing unit. The detailed description of the slim visualization module 100 will be made later with reference to FIGS. 2 to 9.

The content control unit 200 adaptively generates and provides a virtual-reality image to be output through the slim visualization module 100 so that the virtual-reality image matches the training situation. Here, the content control unit 200 may be implemented as a backpack PC worn on the user's body or as a remote wireless connection-type virtual reality content operating server.

In an embodiment, the content control unit 200 analyzes a state image of an external device acquired by the state information acquisition unit 300, generates an image corresponding to virtual-reality environment information, and inputs the generated image to the slim visualization module 100. That is, the content control unit 200 analyzes an image acquired by capturing a measuring instrument (gauge) for outputting the current state of the realistic equipment, such as the breathing air cylinder 4, for example, the state of the remaining amount of air, and then generates a virtual reality image corresponding to the state of the remaining amount of air based on the analyzed image.

The state information acquisition unit 300 may acquire the state of the external device as an image. That is, the state information acquisition unit 300 may acquire the state of the external device such as the breathing air cylinder 4 monitored by an external device state information output unit 320 present in the real space, that is, measurement information such as the remaining amount of air in the form of an image. For example, although the breathing air cylinder 4 is illustrated in FIG. 1, this is only an example provided for a better understanding of the invention, and the present invention is not limited thereto.

Additionally, the state information acquisition unit 300 may further acquire state information measured by a user biometric information output unit 310 which collects biometric signal information of the user.

The configurations and operations of the state information acquisition unit 300 and the content control unit 200 which operates in conjunction with the state information acquisition unit 300 will be described in detail later with reference to FIGS. 10 to 12.

Then, with reference to FIGS. 2 to 11, the slim visualization module 100 according to an embodiment will be described below.

In conventional virtual-reality firefighting training, an HMD is mainly used as a virtual-reality interface, wherein a trainee must simultaneously wear the HMD and a respirator.

Figure 2:
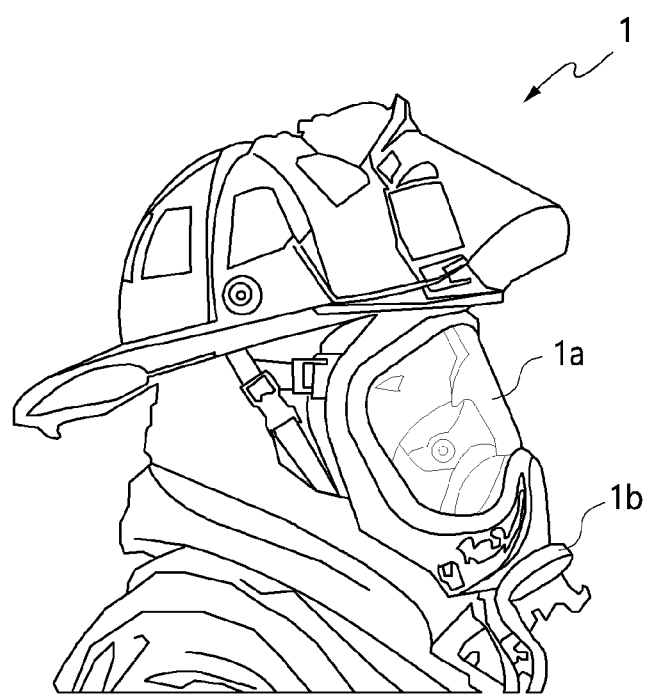
FIG. 2 is a view illustrating an example in which a positive pressure respirator is worn.

FIG. 2 is a diagram illustrating an example in which a positive pressure respirator (or a Self-Contained Breathing Apparatus: SCBA) is worn.

Referring to FIG. 2, a positive pressure respirator 1 is equipment in which pressure within a facepiece is higher than that outside to prevent harmful gas from flowing into the positive-pressure respirator, and in which ON/OFF switching of a respirator valve is controlled so as to maintain uniform air pressure depending on the breathing capacity of each user, thus protecting users (firefighters).

The positive pressure respirator 1 is manufactured such that a transparent visor 1*a* for covering the entire facial area and a respirator 1*b* are integrated with each other. However, an HMD has a volume that is too large to be worn inside the transparent visor 1*a* of the positive pressure respirator 1, and cannot provide realism when worn outside the positive pressure respirator 1.

Therefore, as precedent cases, in virtual-reality firefighting training, a negative-pressure respirator used for a rescuee, rather than the positive pressure respirator 1 (1*a* and 1*b*) actually used by firefighters, is generally employed due to the problem of simultaneous wearing of the HMD.

Figure 3:
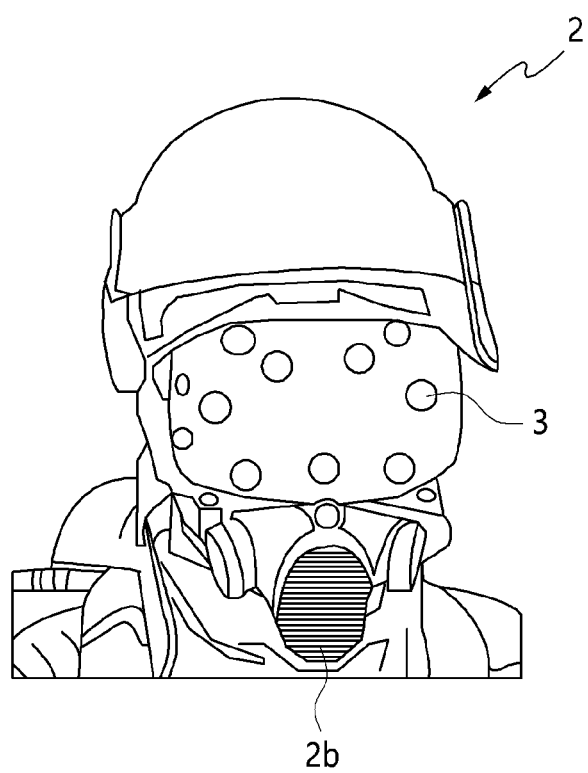
FIG. 3 is a view illustrating an example in which an HMD for virtual-reality training and a negative-pressure respirator are worn.

FIG. 3 is a view illustrating an example in which an HMD for virtual-reality training and a negative-pressure respirator are worn.

Referring to FIG. 3, a negative-pressure respirator 2 has an open facepiece, and thus a user may wear the HMD through the open facepiece. Because the negative-pressure respirator 2 is operated in a scheme in which, when the user inhales air, a respirator 2*b* is opened, there is the possibility that external harmful gas will enter into the respirator 2*b*.

Therefore, when virtual-reality firefighting training is conducted using the negative-pressure respirator 2, a firefighter cannot experience the same breathing sensation as that at the scene of a fire. That is, the difference from the sensation felt by the firefighter when the positive pressure respirator 1 (1*a* and 1*b*) actually used at the scene of a fire is employed may be large.

Accordingly, virtual-reality firefighting training employing the negative-pressure respirator 2 may be suitable for demonstration of training provided to amateurs other than firefighters in such a way that the negative-pressure respirator 2 is utilized in conjunction with field equipment, but may be unsuitable for firefighters who must, through training, obtain experience and capability to respond to actual fires.

Figure 4:
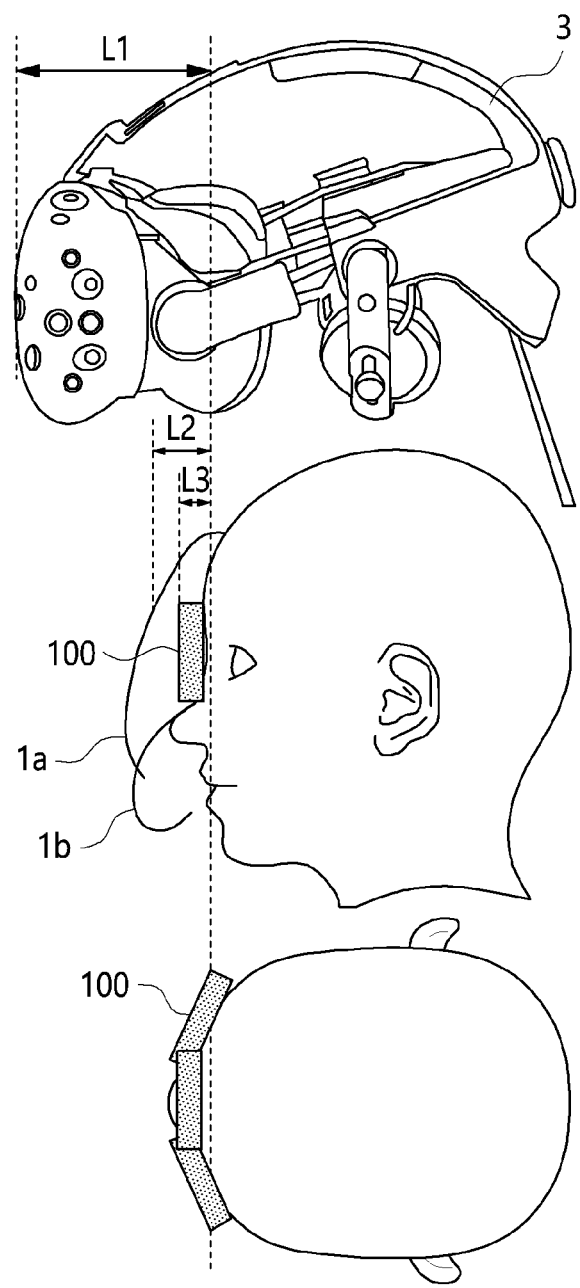
FIG. 4 illustrates a side view and a top view showing the state in which a slim visualization module is worn according to an embodiment.
Figure 5:
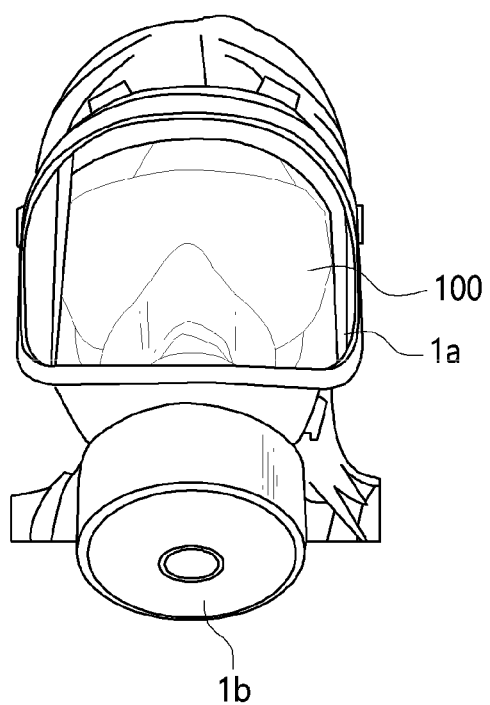
FIG. 5 is a front view showing the state in which a slim visualization module is worn according to an embodiment.

FIG. 4 illustrates a side view and a top view showing the state in which a slim visualization module is worn according to an embodiment, and FIG. 5 is a front view showing the state in which the slim visualization module is worn according to an embodiment.

As illustrated in FIG. 4, a commercial HMD 3 is manufactured with a relatively large thickness L1 from a facial area of a user around the eyes, and thus the thickness L1 is much greater than the allowable space thickness L2 of the transparent visor 1*a* of a positive-pressure respirator.

Therefore, the slim visualization module 100 according to the embodiment is manufactured with a thickness L3 less than the allowable space thickness L2, for example, in a slim shape resembling that of an eye patch coming into close contact with the eyes of the user shown in FIG. 5, and thus the slim visualization module 100 should be able to be worn in the transparent visor 1*a* of the positive pressure respirator 1 (1*a* and 1*b*).

Figure 6:
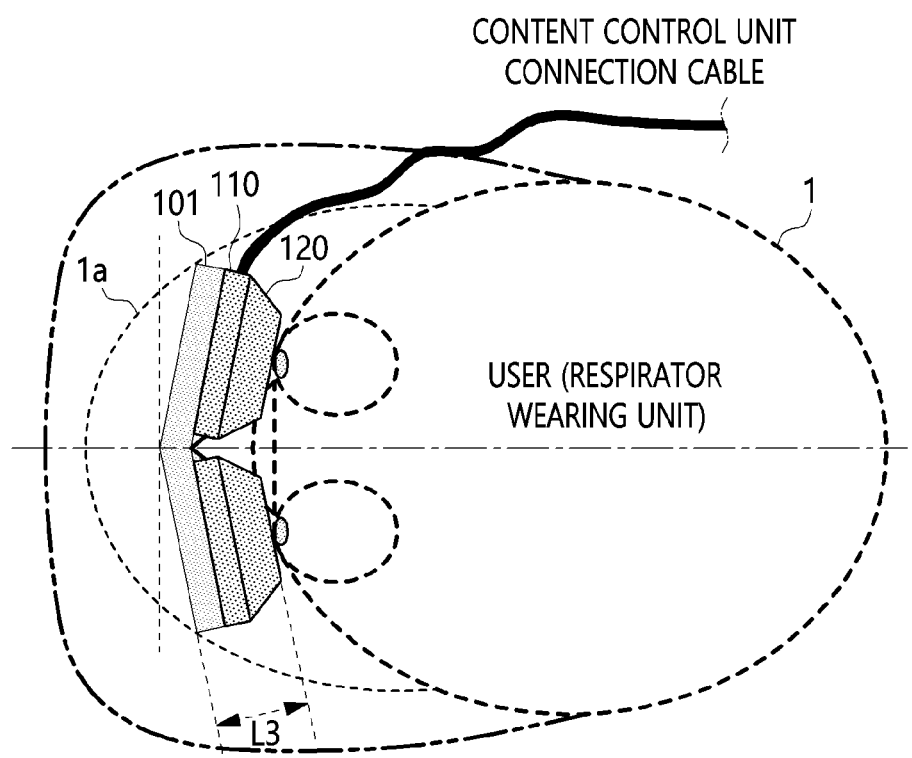
FIG. 6 is a view illustrating in detail a slim visualization module according to an embodiment.
Figure 7:
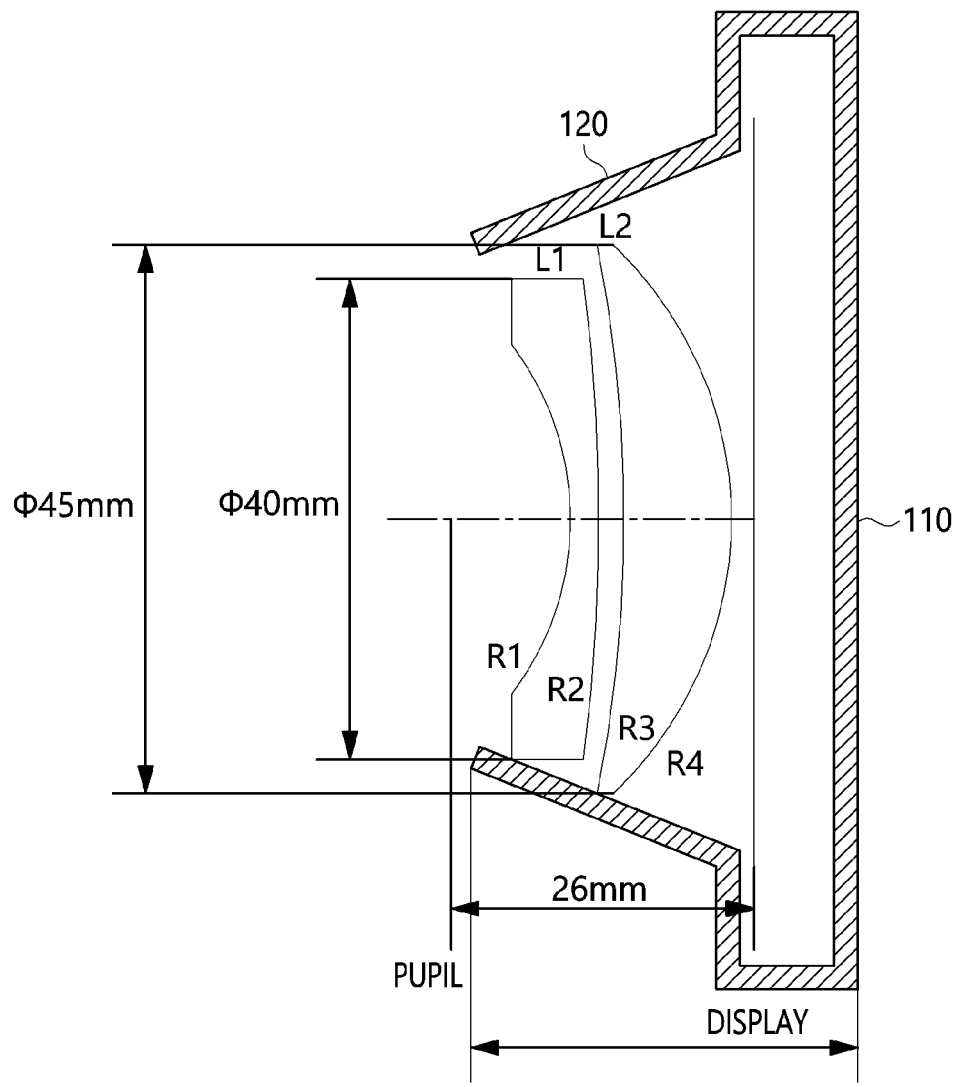
FIG. 7 is a configuration diagram of a display panel and an optical unit included in the slim visualization module according to an embodiment.
Figure 8:
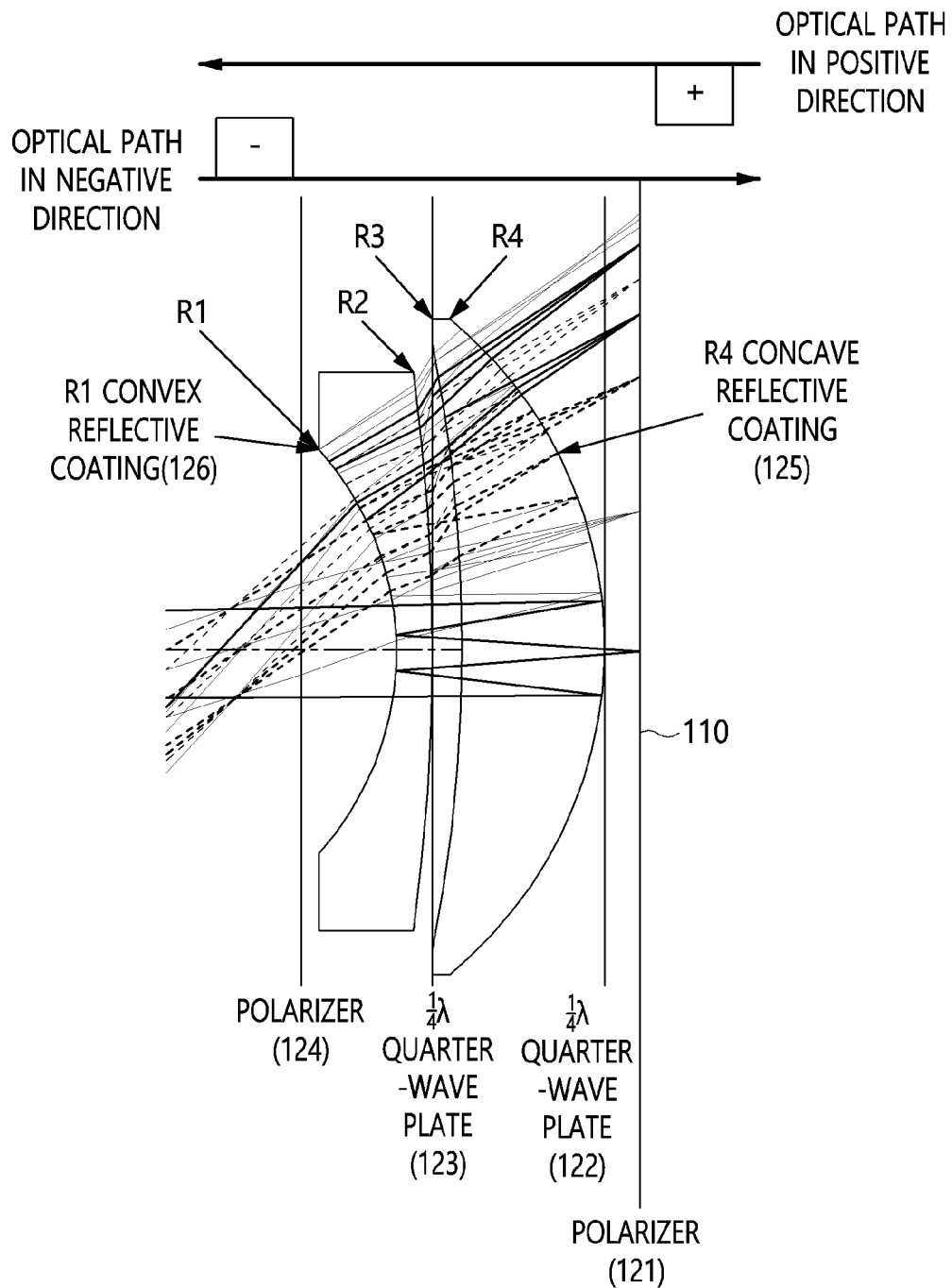
FIG. 8 is a diagram illustrating an example of an optical path in the optical unit according to an embodiment.

FIG. 6 is a view illustrating in detail a slim visualization module according to an embodiment, FIG. 7 is a configuration diagram of a display panel and an optical unit included in the slim visualization module according to an embodiment, and FIG. 8 is a diagram illustrating an example of an optical path in the optical unit according to an embodiment.

Referring to FIGS. 6 and 7, a slim visualization module 100 according to an embodiment may include a display panel 110 and an optical unit 120.

Further, although not illustrated in the drawings, the slim visualization module 100 may be configured such that the display panel 110 and the optical unit 120 are mounted in a module body and such that a band or a fastener is coupled to both ends of the module body to enable the module body to be fixed at the circumference of the user's head or ears in the state in which the module body covers the eyes.

The display panel 110 is a means for outputting an image generated by the content control unit 200, and may be provided as one of parts of a wearable display panel including a Liquid Crystal Display (LCD), Liquid Crystal on Silicon (LCOS), Digital Light Processing (DLP) or an Organic Light-Emitting Diode (OLED).

However, when the display panel 110 is brought within a distance of about 10 cm or less from the eyeball of the user, a person having normal eyesight condition cannot clearly view the image output via the display panel 110 due to the limited accommodation power of a crystalline lens. Therefore, technology for additionally providing the optical unit 120 between the display panel and the eyeball of the user and visualizing an image on the display panel, which is positioned physically close to the eyeball, as a virtual image spaced apart from the display panel by a predetermined distance (e.g., 2 to 3 in) has been applied to a commercial HMD (e.g., Oculus RIFT and HTC VIVE).

The present embodiment is intended to structurally design a slim visualization module 100, which has a thickness L3 at which the module can be accommodated in the internal space of a small facepiece-shaped visor, having a thickness L2 less than the thickness L1 of the conventional HMD, and which can correspond to the features of a human visual system structure (i.e., a human factor).

For this, the optical unit 120 according to an embodiment is manufactured using at least two refractive lenses, and is configured to refract and reflect straight-traveling visible light corresponding to an image output via the display panel 110 through the two or more refractive lenses, thus forming the image on the retina of the eyeball of the user.

The optical unit of the conventional commercial HMD has a thickness of about 60 mm or more because it is implemented using a single lens in most cases. Therefore, in the embodiment, in order to realize a slim structure having a thickness of 30 mm or less, a path of visible light that travels straight is shortened using at least two refractive lenses.

Below, an embodiment of the optical unit 120 composed of two lenses will be described with reference to FIGS. 7 and 8. However, this is only an embodiment, and the number of lenses constituting the optical unit 120 is not limited to 2.

Referring to FIG. 7, the optical unit 120 according to the embodiment may be composed of a first lens L1 having a first surface R1 facing the retina of the eyeball of a user and a second lens L2 having a first surface R3 facing a second surface R2 of the first lens L1 and a second surface R4 facing the display panel 110.

Here, each of the first lens L1 and the second lens L2 may be made of a material having a refractive index of about 1.5 to 1.7.

Here, the optical unit 120 may have a structure in which the curvature of the first surface R1 of the first lens L1 is less than that of the second surface R2 of the first lens L1 and the curvature of the second surface R4 of the second lens L2 is less than that of the first surface R3 of the second lens L2.

In an example, the curvatures of respective curved surfaces may be designed to have values falling within a range from −5% to +5% of the values given in the following Table 1.

TABLE 1

| Curved surface | Curvature |
| --- | --- |
| R1 | 25 |
| R2 | 134.75 |
| R3 | 121.89 |
| R4 | 32.25 |

Therefore, as illustrated in FIG. 8, visible light corresponding to an image output from the display panel 110 is primarily refracted while sequentially passing through the second lens L2 and the first lens L1. Then, the primarily refracted visible light is reflected from the first surface R1 of the first lens L1, and is then secondarily refracted while sequentially passing through the first lens L1 and the second lens L2. For this operation, a convex reflective coating 126 may be applied onto the first surface R1 of the first lens L1.

Thereafter, the secondarily refracted visible light may be reflected from the second surface R4 of the second lens L2, may be tertiarily refracted while sequentially passing through the second lens L2 and the first lens L1, and may then be delivered to the pupil of the user. For this, in an example, a concave reflective coating 125 may be applied onto the second surface R4 of the second lens L2.

By means of this structure, in comparison with the case where a commercial HMD implemented as a single lens requires an optical path length of at least about 50 mm or more from the display panel 110 to the pupil, the optical unit 120 according to the embodiment forms an optical path through which light passes through the lenses a total of six times by utilizing at least two lenses, thus shortening the length of a physical optical path to about 25 mm or less. That is, compared to the conventional commercial HMD, the length of the optical path may be reduced by more than half, with the result that a slim optical unit 120 may be realized.

Here, the design and simulation of the optical unit 120 according to the embodiment are conducted using "Code V" and "Light Tools", and a viewing angle may be designed to be optimized to a value exceeding 100°, similar to a commercial HMD.

Meanwhile, in the optical unit 120 implemented in a slim structure, such as that illustrated in FIG. 7, a multi-overlapping image effect caused by re-reflection may occur. In order to reduce such a negative effect, when polarized light is not output from the display panel 110 (e.g., an OLED panel), as in the case of an LCD, the optical unit 120 according to the embodiment may be configured using ¼-wavelength phase retarders (i.e., quarter-wave retarders or quarter-wave plates) together with multiple polarizing filters (polarizers).

That is, referring to FIG. 8, the optical unit 120 according to the embodiment may further include a polarizing filter (polarizer) 121 disposed between the display panel 110 and the second lens L2, a ¼-wavelength phase retarder (quarter-wave plate) 122 disposed between the polarizer 121 and the second lens L2, a quarter-wave plate 123 disposed between the second lens L2 and the first lens L1, and a linear polarizer 124 disposed between the first lens L1 and the retina of the eyeball of the user.

Such an optical filter (e.g., a wave plate) assigns polarization properties to light generated from the display panel 110, and changes the properties of light through a procedure in which light passes through multiple filters and is reflected, and thus light starting from the display panel 110 ultimately reaches the user's eyes while passing through a path corresponding to a distance exceeding the thickness of the physical lens module. In this way, the effect of forming an extended optical system may be yielded.

The order and path in which light travels in the optical unit 120, configured as illustrated in FIG. 8, may be summarized, as shown in the following Table 2.

TABLE 2

0. Light starts from an image panel (positive [+] direction).
1. Light passes through the P-polarizer 121, and polarized light is generated (P-polarization).
2. [+] Light passes through the ¼ λ retarder 122, and left-hand circularly polarized light is generated (C-polarization).
3. [+] Light passes through the lens curved surface R4, and refracted light is generated.
4. [+] Light passes through the lens curved surface R3, and refracted light is generated.
5. [+] Light passes through the ¼λ retarder 123, and polarized light is generated (S-polarization).
6. [+] Light passes through the lens curved surface R2, and refracted light is generated.
7. Light is reflected from the convex surface 126 of R1, and polarization phase is inverted (S'-polarization).
8. [−] Light passes through the lens surfaced surface R2, and refracted light is generated.
9. [−] Light passes through the ¼λ retarder 123, and circularly polarized light is generated (C-polarization).
10. [−] Light passes through the lens curved surface R3, and refracted light is generated.
11. [−] Light is reflected from the concave surface 125 of R4, and phase-inverted circularly polarized light is generated (C"-polarization).
12. [+] Light passes through the lens curved surface R3, and refracted light is generated.
13. [+] Light passes through the ¼λ retarder 123, and polarized light is generated (P"-

TABLE 2-continued polarization).
14. [+] Light passes through the lens curved surface R2, and refracted light is generated.
15. [+] Light passes through the lens curved surface R1, and refracted light is generated.
16. [+] Light passes through the P-polarizer 124, and only P'''-polarized light ultimately reaches the pupil).

That is, referring to FIG. 8 and Table 2, light initially output from the display panel 110 travels in a direction facing human eyes (hereinafter referred to a 'positive direction'), and polarized light is generated (P-polarization) while the traveling light passes through the P-polarizer 121. Thereafter, left-hand circularly polarized light is generated (C-polarization) while the polarized light passes through the quarter-wave plate 122. Thereafter, the light continues to travel in the positive direction, and is then refracted while sequentially passing through the curved surface R4 and the curved surface R3 of the second lens L2. Thereafter, polarized light is generated (S-polarization) while the refracted light passes through the quarter-wave plate 123. The generated polarized light is refracted while passing through the curved surface R2 of the first lens L1, the refracted light is reflected from the convex surface of the curved surface R1 of the first lens L1, and then the phase of the polarized light (polarization phase) is inverted (S'-polarization). That is, the phase of the light continuing to travel in the positive direction from the display panel 110 is inverted to a negative direction which is the opposite direction of the curved surface R1 of the first lens L1.

Thereafter, light traveling in the negative direction is refracted while passing through the curved surface R2 of the first lens L1, and circularly polarized light is generated (C'-polarization) while the refracted light passes through the quarter-wave plate 123. Thereafter, the circularly polarized light is refracted while passing through the curved surface R3 of the second lens L2. The refracted light continues to travel in the negative direction and is reflected from the concave surface of the curved surface R4 of the second lens L2, and then phase-inverted circularly polarized light is generated (C"-polarization). That is, the phase of light that is reflected from the convex surface of the curved surface R1 of the first lens L1 and then continues to travel in the negative direction is inverted back to the positive direction, which is the opposite direction, on the curved surface R4 of the second lens L2.

Then, the light traveling in the positive direction is refracted while passing through the curved surface R3 of the second lens L2, and polarized light is generated (P'''-polarization) while the refracted light passes through the quarter-wave plate 123. Thereafter, light is refracted while passing through the curved surface R2 of the first lens L1, and is then refracted while passing through the curved surface R1 of the first lens L1. Finally, the light continues to travel in the positive direction and passes through the P-polarizer, and P-polarized light ultimately reaches the pupil of the user.

Meanwhile, the slim visualization module 100 according to the embodiment may be implemented as an integrated module into which the display panel 110 and the optical unit 120 are integrated with each other, wherein the module may be separated into a left-eye module and a right-eye module to correspond to the left eye and the right eye, respectively.

Figure 9:
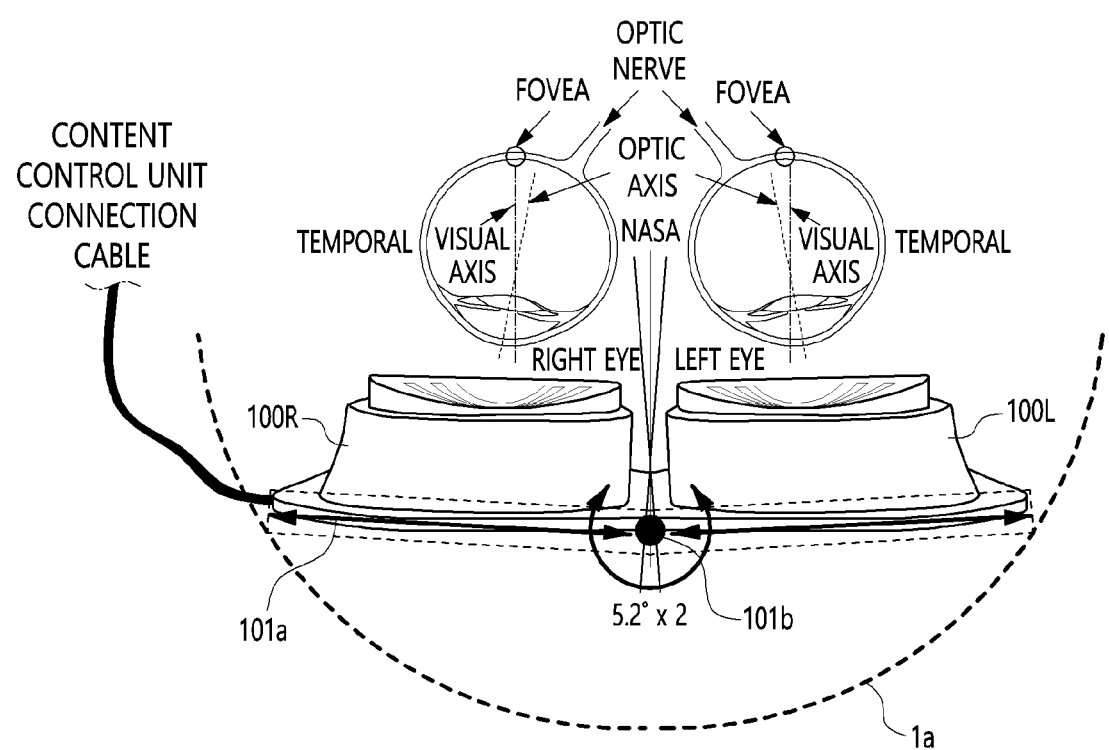
FIG. 9 is a view illustrating the configuration of a binocular slim visualization module according to an embodiment.

FIG. 9 is a configuration diagram of a binocular slim visualization module according to an embodiment.

Referring to FIG. 9, in each of a right-eye module 100R and a left-eye module 100L, a display panel 110 and an optical unit 120 may be mounted in a facepiece to have a structure matching a corresponding one of the left and right eyes.

Here, the binocular slim visualization module according to the embodiment may further include an interpupillary distance (or an inter-pupil distance) (IPD) adjustment unit 101a for adjusting the distance between the right-eye module 100R and the left-eye module 100L.

Here, the interpupillary distance adjustment unit 101a is implemented in the form of a slide, and may have a structure for adjusting the distance in such a way that each of the right-eye module 100R and the left-eye module 100L slidably moves to the left and right on the slide.

By means of this configuration, a binocular stereoscopic image in which the user's visual properties (human factor) covering a wide range are taken into consideration may be implemented. In addition, there is an advantage in that when the slim visualization module is arranged in narrow space within the facepiece of the respirator, additional space may be secured.

The binocular slim visualization module according to the embodiment may further include an interpupillary angle adjustment unit 101b for adjusting a joint angle between the right-eye module 100R and the left-eye module 100L.

According to anatomical data on human visual sensory organs, it is known that the optical axis of the eyeball and a visual axis depending on the distribution of retinal optic nerves has an angular difference of about 5.2° therebetween. Therefore, the interpupillary angle adjustment unit 101b may be manufactured with a structure using multiple combined gears or a hinge-coupling structure, and may then be folded at an angle of about 0 to 10°, thus enabling a binocular immersive display corresponding to a wide range of human visual properties (human factor) to be implemented.

Therefore, since the interpupillary distance has an average distance of about 65 mm according to statistical data, the interpupillary distance and the interpupillary angle may be changed within a variable range from −10~20% to +10~20% of the average value through the above-described interpupillary distance adjustment unit 101a and the interpupillary angle adjustment unit 101b.

Meanwhile, the interpupillary distance adjustment unit 101a and the interpupillary angle adjustment unit 101b may be manually controlled by the user, but may be automatically controlled in response to a signal output from the content control unit 200. For example, the content control unit 200 may automatically and precisely control the interpupillary distance adjustment unit 101a and the interpupillary angle adjustment unit 101b so that they are optimized for the user based on user state information.

Figure 10:
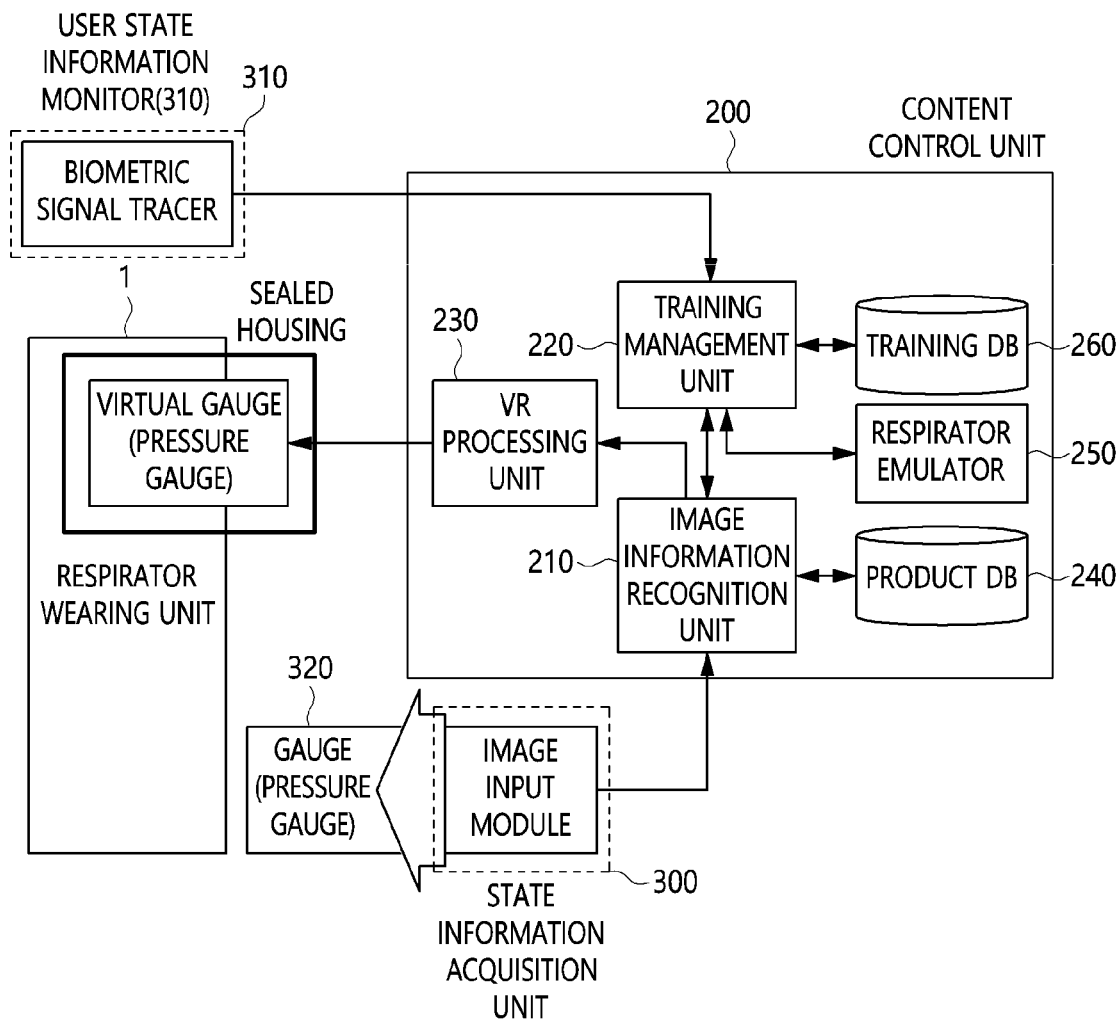
FIG. 10 is a configuration diagram illustrating interoperation between a content control unit and a state information acquisition unit according to an embodiment.
Figure 11:
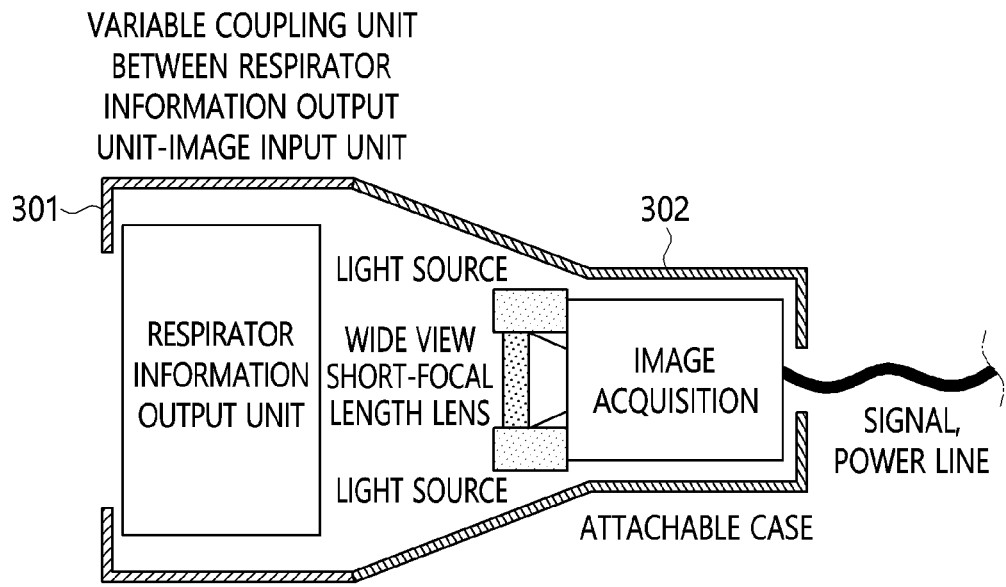
FIGS. 11 and 12 are configuration diagrams of a state information acquisition unit according to an embodiment.
Figure 12:
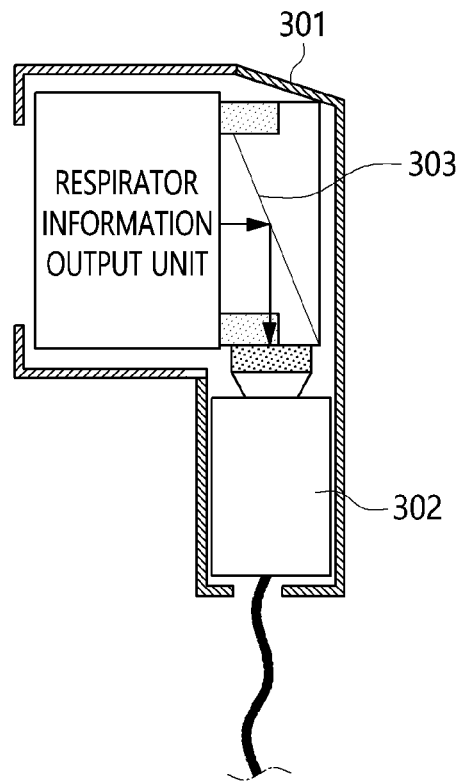

FIG. 10 is a configuration diagram illustrating interoperation between a content control unit and a state information acquisition unit according to an embodiment, and FIGS. 11 and 12 are configuration diagrams of the state information acquisition unit according to an embodiment.

Referring to FIG. 10, in order to utilize actual equipment used on site for virtual-reality training, technology for associating an output value, obtained by measuring the actual equipment, with virtual-reality content in real time is required. For example, when the actual equipment is a breathing air cylinder 4, as illustrated in FIG. 1, a numerical value such as the air pressure or the remaining amount of air in the breathing air cylinder 4 must be associated with virtual-reality content in real time.

However, because the user who uses a virtual training system is blocked from observing the external environment due to wearing of the HMD, a module for acquiring information output from a measuring instrument which measures the actual equipment is required.

Meanwhile, in the case of facepiece respirators for firefighting sites, most devices (gauges) for displaying the current pressure of an air tank are implemented using a graduated-type analog scheme, and some devices are implemented in a hybrid scheme combined with a digital indicator. Further, in the case of respirators for firefighting sites, there are multiple foreign manufacturers in addition to domestic manufacturers, and devices for respective manufacturers have their own unique interface shapes.

Therefore, in order to associate the current state information of actual equipment using various schemes and various interface shapes with computer-based virtual-reality training content, state information of the actual equipment must be able to be digitized.

Therefore, the present invention proposes a state information acquisition unit capable of capturing images of pressure gauges so that pieces of information from various analog-based or analog-digital hybrid pressure gauges can be recognized so as to implement existing firefighting equipment in the form of a virtual-reality interface.

Referring to FIG. 11, a state information acquisition unit 300 may include a coupling unit 301 which is attached to and detached from a respiratory information output unit which is the information output unit of an external device, and an image acquisition unit 302 which acquires a short-range image of the external device.

In this case, the coupling unit 301 may be made of a magnet and a flexible material. For example, as a coupling structure attachable/detachable to/from various pressure gauges, the coupling unit 301 may be manufactured using, for example, a magnet, an integrated case made of a flexible material (e.g., rubber or silicon) corresponding to an arbitrary shape, Velcro, a belt, or the like.

The image acquisition unit 302 may be attached to the surface of the gauge, and may have a structure that is easily removable together with a light source unit (e.g., a Light-Emitting Diode (LED) light source.

Here, the image acquisition unit 302 may implement close-up image capture using a Universal Serial Bus (USB) camera or the like, having a size less than that of a Korean 100-won coin.

In this case, in accordance with an embodiment, the image acquisition unit 302 may be installed in a direction parallel to the pressure gauge, as illustrated in FIG. 11.

Further, in another embodiment, the image acquisition unit 302 may be installed in a direction perpendicular to the pressure gauge, as illustrated in FIG. 12. In this case, as illustrated in FIG. 12, a reflective mirror 303 may be further arranged between the coupling unit 301 and the image acquisition unit 302, and may be configured to vertically reflect an image displayed on the respirator information output unit and to input the reflected image to the image acquisition unit 302.

Referring back to FIG. 10, the content control unit 200 may include an image information recognition unit 210, a training management unit 220, and a virtual-reality processing unit 230.

The image information recognition unit 210 recognizes information on an external device from the state image of the external device received from the state information acquisition unit 300.

The image information recognition unit 210 may implement state images for respective product types of external devices through a model previously learned based on machine learning such as pattern recognition, or may implement the state images using traditional image-processing technology.

For this, the content control unit 200 may further include a product database (DB) 240 in which information required to recognize images corresponding to commercial products of external devices can be constructed in advance.

The training management unit 220 updates the state of a virtual object with the result of simulation of a function of the virtual object in virtual-reality content based on the information on an external device recognized by the image information recognition unit 210.

That is, the training management unit 220 simulates virtual-reality content stored in the training DB 260 using the respirator emulator 250 based on the recognized external device information, updates the states of various objects included in the virtual-reality content based on the results of simulation, and again stores the updated states in the training DB 260. Further, the training management unit 220 quotes a preliminary training scenario stored in the training DB 260, or records a current training change procedure in the training DB 260.

The virtual-reality processing unit 230 may process image information of the content in which the states of virtual objects are updated as virtual-reality image information, and may output the processed image information to the slim visualization module 100.

For example, the virtual-reality processing unit 230 may modify the state of a respirator wearing unit indicated by the gauge 320 into virtual gauge values corresponding to various visual expressions, rather than simply indicating the state by a numerical value, and may output the gauge values to the slim visualization module 100.

Meanwhile, the state information acquisition unit 300 may further collect biometric signal information of the user.

Then, the content control unit 200 may further incorporate the user's biometric signal information into content. That is, the information collected by the training management unit may be the user's biometric signal information (e.g., a body temperature, a heart rate, the level of tension, etc.), and may be utilized to update the virtual content.

Figure 13:
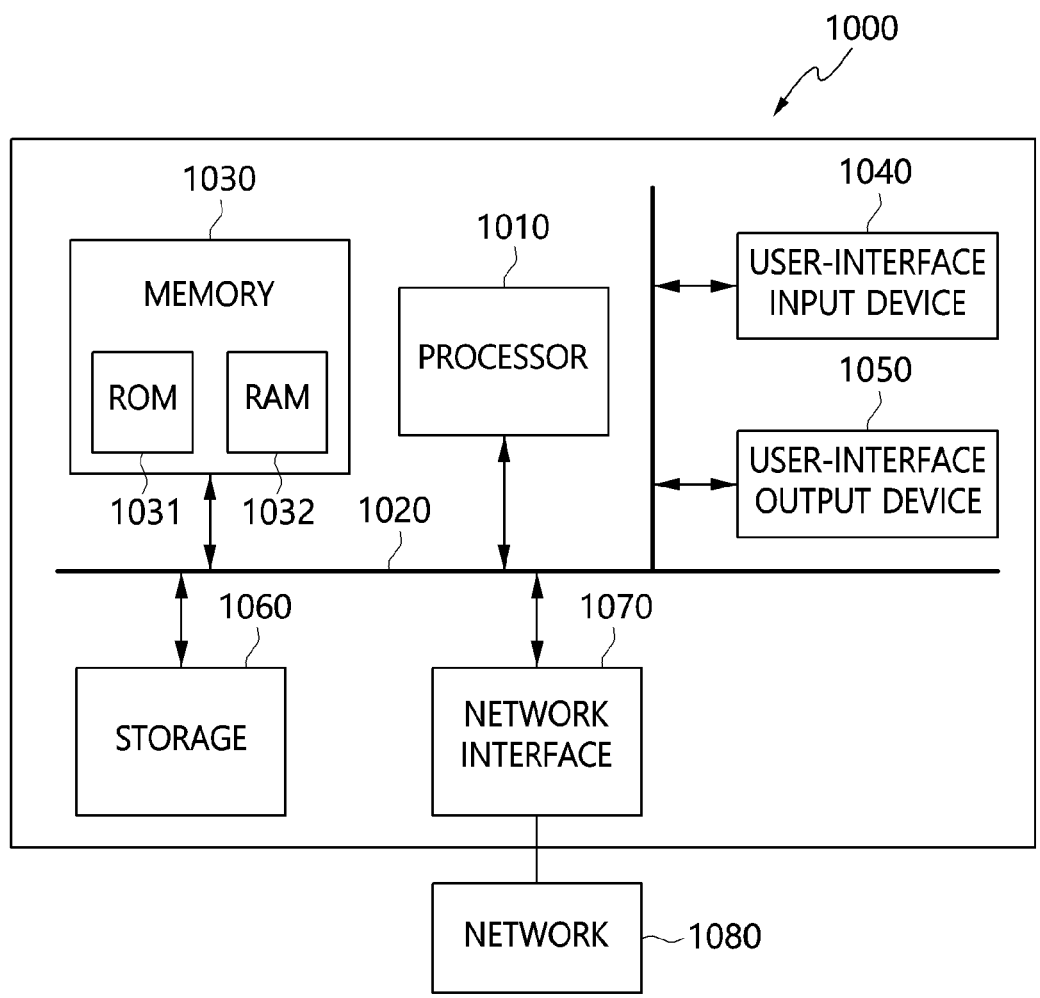
FIG. 13 is a diagram illustrating the configuration of a computer system according to an embodiment.

FIG. 13 is a diagram illustrating the configuration of a computer system according to an embodiment.

The content control unit 200 according to the embodiment may be implemented in a computer system 1000 such as a computer-readable storage medium.

The computer system 1000 may include one or more processors 1010, memory 1030, a user interface input device 1040, a user interface output device 1050, and storage 1060, which communicate with each other through a bus 1020. The computer system 1000 may further include a network interface 1070 connected to a network 1080. Each processor 1010 may be a Central Processing Unit (CPU) or a semiconductor device for executing programs or processing instructions stored in the memory 1030 or the storage 1060. Each of the memory 1030 and the storage 1060 may be a storage medium including at least one of a volatile medium, a nonvolatile medium, a removable medium, a non-removable medium, a communication medium, or an information delivery medium. For example, the memory 1030 may include Read-Only Memory (ROM) 1031 or Random Access Memory (RAM) 1032.

In accordance with an embodiment, there is an advantage in that a display device for presenting an immersive image having a viewing angle (field of view) of about 100° can be constructed in space within a distance of a few tens of mm from the eyes of a user. Therefore, the user can wear additional equipment related to a facepiece, such as a respirator.

In accordance with an embodiment, a slim visualization interface and technology for acquiring and associating equipment state information has an advantage of maintaining the same sense of realism as that pursued by a normal training system, thus improving the effect of a training system.

A visualization module according to an embodiment may be universally utilized as technology for implementing an interface which maintains the sense of using equipment (e.g., a positive-pressure respirator) at an actual site when implementing a virtual training system which takes into consideration situations in which face-mask-type respirators, employed in various fields, such as firefighting, military, medical, safety, and disease prevention fields, are used.

Although the embodiments of the present invention have been disclosed with reference to the attached drawing, those skilled in the art will appreciate that the present invention can be implemented in other concrete forms, without changing the technical spirit or essential features of the invention. Therefore, it should be understood that the foregoing embodiments are merely exemplary, rather than restrictive, in all aspects.

What is claimed is:

1. A slim visualization device, comprising:
a display panel configured to output an externally input image signal; and
an optical unit manufactured using at least two refractive lenses and configured to refract and reflect straight-traveling visible light corresponding to an image output via the display panel through the at least two refractive lenses, thus forming the image on a retina of an eyeball of a user,
wherein the optical unit comprises:
a first lens having a first surface facing the retina of the eyeball of the user;
a second lens having a first surface facing a second surface of the first lens and a second surface facing the display panel,
wherein the first lens is concave in shape, and the second lens is convex in shape, and
wherein a curvature of the first surface of the first lens is less than a curvature of the second surface of the first lens, and a curvature of the second surface of the second lens is less than a curvature of the first surface of the second lens,
wherein the optical unit further comprises:
a convex reflective coating applied onto the first surface of the first lens;
a concave reflective coating applied onto the second surface of the second lens;
a polarizer disposed between the display panel and the second lens;
a quarter-wave plate disposed between the polarizer and the second lens;
a quarter-wave plate disposed between the second lens and the first lens; and
a linear polarizer disposed between the first lens and the eyeball of the user, and
wherein the optical unit is configured such that:
the visible light corresponding to the image output via the display panel is primarily refracted while sequentially passing through the second lens and the first lens toward the eyeball of the user,
the primarily refracted visible light is reflected from the first surface of the first lens, and is secondarily refracted while sequentially passing through the first lens and the second lens toward the display panel, and
the secondarily refracted visible light is reflected from the second surface of the second lens, is tertiarily refracted while sequentially passing through the second lens and the first lens toward the eyeball of the user, and is then delivered to a pupil of the user.

2. The slim visualization device of claim 1, wherein:
a refractive index of each of the first lens and the second lens is designed to have a value falling within a range from 1.5 to 1.7,
the curvature of the first surface of the first lens is designed to have a value falling within a range from −5% to +5% of 25,
the curvature of the second surface of the first lens is designed to have a value falling within a range from −5% to +5% of 134.75,
the curvature of the first surface of the second lens is designed to have a value falling within a range from −5% to +5% of 121.89, and
the curvature of the second surface of the second lens is designed to have a value falling within a range from −5% to +5% of 32.25.

3. The slim visualization device of claim 1, wherein:
the display panel and the optical unit are implemented as an integrated module,
the integrated module is separated into a left-eye module and a right-eye module to correspond to a left eye and a right eye of the user, respectively, and
the slim visualization device further comprises an interpupillary distance adjustment unit for adjusting a distance between the left-eye module and the right-eye module.

4. The slim visualization device of claim 1, wherein:
the display panel and the optical unit are implemented as an integrated module,
the integrated module is separated into a left-eye module and a right-eye module to correspond to a left eye and a right eye, respectively, and
the slim visualization device further comprises an interpupillary angle adjustment unit for adjusting a joint angle between the right-eye module and the left-eye module.

5. A slim immersive display device, comprising:
a slim visualization module for forming an image on a retina of an eyeball of a user based on an externally input image signal;
a state information acquisition unit for acquiring a state of an external device as a state image; and
a content control unit for analyzing the state image, generating an image corresponding to virtual-reality environment information based on the analyzed state image, and inputting the image to the slim visualization module,
wherein the content control unit comprises:

an image information recognition unit configured to be learned in advance based on state images for respective product types of the external device, and to recognize information on the external device from the state image input from the state information acquisition unit;

a training management unit configured to simulate virtual-reality content stored in a training database using the information on the external device recognized by the image information recognition unit, and to update states of a plurality of virtual objects included in the virtual-reality content with a result of the simulating; and a virtual-reality processing unit configured to process image information of the virtual-reality content, in which the states of the plurality of virtual object are updated, as virtual-reality image information, and to output the processed virtual-reality image information to the slim visualization module, wherein the slim visualization module comprises:
a display panel configured to output the externally input image signal; and
an optical unit manufactured using at least two refractive lenses and configured to refract and reflect straight-traveling visible light corresponding to an image output via the display panel through the at least two refractive lenses, thus forming the image on the retina of the eyeball of the user, wherein the optical unit comprises:
a first lens having a first surface facing the retina of the eyeball of the user; and
a second lens having a first surface facing a second surface of the first lens and a second surface facing the display panel,
wherein a curvature of the first surface of the first lens is less than a curvature of the second surface of the first lens, and a curvature of the second surface of the second lens is less than a curvature of the first surface of the second lens, and
wherein the first lens is concave in shape, and the second lens is convex in shape, wherein the optical unit further comprises:
a convex reflective coating applied onto the first surface of the first lens;
a concave reflective coating applied onto the second surface of the second lens;
a polarizer disposed between the display panel and the second lens;
a quarter-wave plate disposed between the polarizer and the second lens;
a quarter-wave plate disposed between the second lens and the first lens; and
a linear polarizer disposed between the first lens and the eyeball of the user, and wherein the optical unit is configured such that:
the visible light corresponding to the image output via the display panel is primarily refracted while sequentially passing through the second lens and the first lens toward the eyeball of the user,
the primarily refracted visible light is reflected from the first surface of the first lens, and is secondarily refracted while sequentially passing through the first lens and the second lens toward the display panel, and
the secondarily refracted visible light is reflected from the second surface of the second lens, is tertiarily refracted while sequentially passing through the second lens and the first lens toward the eyeball of the user, and is then delivered to a pupil of the user.

6. The slim immersive display device of claim 5, wherein the state information acquisition unit comprises:
a coupling unit attached/detached to/from an information output unit for sensing the external device; and
an image acquisition unit for acquiring a short-range image of the information output unit for sensing the external device.

7. The slim immersive display device of claim 6, wherein the coupling unit is made of a magnet and a flexible material.

8. The slim immersive display device of claim 5, wherein:
the state information acquisition unit further acquires a state image of an information output unit for collecting biometric signal information of the user, and
the content control unit incorporates the biometric signal information of the user into the virtual-reality content.

9. The slim immersive display device of claim 5, wherein:
a refractive index of each of the first lens and the second lens is designed to have a value falling within a range from 1.5 to 1.7,
the curvature of the first surface of the first lens is designed to have a value falling within a range from −5% to +5% of 25,
the curvature of the second surface of the first lens is designed to have a value falling within a range from −5% to +5% of 134.75,
the curvature of the first surface of the second lens is designed to have a value falling within a range from −5% to +5% of 121.89, and
the curvature of the second surface of the second lens is designed to have a value falling within a range from −5% to +5% of 32.25.

10. The slim immersive display device of claim 5, wherein:
the display panel and the optical unit are implemented as an integrated module,
the integrated module is separated into a left-eye module and a right-eye module to correspond to a left eye and a right eye of the user, respectively, and
the slim visualization module further comprises an inter-pupillary distance adjustment unit for adjusting a distance between the left-eye module and the right-eye module.

11. The slim immersive display device of claim 5, wherein:
the display panel and the optical unit are implemented as an integrated module,
the integrated module is separated into a left-eye module and a right-eye module to correspond to a left eye and a right eye of the user, respectively, and
the slim visualization module further comprises an inter-pupillary angle adjustment unit for adjusting a joint angle between the right-eye module and the left-eye module.

12. A slim immersive display device, comprising:
a slim visualization module for forming an image on a retina of an eyeball of a user based on an externally input image signal;
a state information acquisition unit for acquiring a state image of an information output unit for sensing an external device; and
a content control unit for analyzing the state image, generating an image corresponding to virtual-reality environment information, and inputting the image to the slim visualization module;

wherein the slim visualization module comprises:
  a display panel configured to output the externally input image signal; and
  an optical unit manufactured using at least two refractive lenses and configured to refract and reflect straight-traveling visible light corresponding to an image output via the display panel through the at least two refractive lenses, thus forming the image on the retina of the eyeball of the user,
  wherein the at least two refractive lenses comprises:
    a first lens having a first surface facing the retina of the eyeball of the user;
    a second lens having a first surface facing a second surface of the first lens and a second surface facing the display panel,
    wherein the first lens is concave in shape, and the second lens is convex in shape, and
    wherein a curvature of the first surface of the first lens is less than a curvature of the second surface of the first lens, and a curvature of the second surface of the second lens is less than a curvature of the first surface of the second lens,
  wherein the optical unit further comprises:
    a convex reflective coating applied onto the first surface of the first lens;
    a concave reflective coating applied onto the second surface of the second lens;
    a polarizer disposed between the display panel and the second lens;
    a quarter-wave plate disposed between the polarizer and the second lens;
    a quarter-wave plate disposed between the second lens and the first lens; and
    a linear polarizer disposed between the first lens and the eyeball of the user, and
  wherein the optical unit is configured such that:
    the visible light corresponding to the image output via the display panel is primarily refracted while sequentially passing through the second lens and the first lens toward the eyeball of the user,
    the primarily refracted visible light is reflected from the first surface of the first lens, and is secondarily refracted while sequentially passing through the first lens and the second lens toward the display panel, and
    the secondarily refracted visible light is reflected from the second surface of the second lens, is tertiarily refracted while sequentially passing through the second lens and the first lens toward the eyeball of the user, and is then delivered to a pupil of the user.

13. The slim immersive display device of claim 12, wherein the content control unit comprises:
  an image information recognition unit configured to be learned in advance based on state images for respective product types of the external device, and to recognize information on the external device from the state image input from the state information acquisition unit;
  a training management unit configured to simulate virtual-reality content stored in a training database using the information on the external device recognized by the image information recognition unit, and to update states of a plurality of virtual objects included in the virtual-reality content with a result of the simulating; and
  a virtual-reality processing unit configured to process image information of the virtual-reality content, in which the states of the plurality of virtual objects are updated, as virtual-reality image information, and to output the processed virtual-reality image information to the slim visualization module.

\* \* \* \* \*